United States Patent [19]

Loerzer et al.

[11] Patent Number: 4,770,976
[45] Date of Patent: Sep. 13, 1988

[54] PHENANTHROIMIDAZOLE COMPOUNDS, THEIR PREPARATION, PHOTOPOLYMERIZABLE COATING AND RECORDING MATERIALS, AND LITHOGRAPHIC LAYERS PRODUCED USING THESE

[75] Inventors: Thomas Loerzer, Frankenthal; Reinhold J. Leyrer, Ludwigshafen, both of Fed. Rep. of Germany

[73] Assignee: BASF Aktiengesellschaft, Ludwigshafen, Fed. Rep. of Germany

[21] Appl. No.: 28,671

[22] Filed: Mar. 20, 1987

[30] Foreign Application Priority Data

Mar. 20, 1986 [DE] Fed. Rep. of Germany ....... 3609318

[51] Int. Cl.$^4$ .................................... G03C 1/68
[52] U.S. Cl. .................................... 430/281; 430/920; 522/33; 522/39; 522/50; 522/63; 548/114; 548/326
[58] Field of Search ............... 548/114, 326; 522/33, 522/39, 50, 63; 430/920, 281

[56] References Cited

U.S. PATENT DOCUMENTS

| | | | |
|---|---|---|---|
| 3,061,435 | 10/1962 | Tomanek et al. | 96/75 |
| 3,279,918 | 10/1966 | Cassiers et al. | 96/1 |
| 3,429,890 | 2/1969 | Sletzinger et al. | 260/302 |
| 3,597,343 | 8/1971 | Delzenne | 522/63 X |
| 3,962,056 | 6/1976 | Pacifici et al. | 522/63 |
| 4,258,121 | 3/1981 | Kojima | 430/920 X |
| 4,311,783 | 2/1982 | Dessauer | 430/270 |
| 4,456,679 | 6/1984 | Leyrer et al. | 430/326 |
| 4,465,760 | 8/1984 | Leyrer et al. | 430/325 |
| 4,565,771 | 1/1986 | Lynch et al. | 430/307 |
| 4,579,806 | 4/1986 | Schupp et al. | 430/280 |

OTHER PUBLICATIONS

F. J. Allen and G. G. Allan, Chem. Ind. 1964, 1837.
K. Volkamer & H. W. Zimmermann, Chem. Ber. 102 (1969), 4177.
K. Akagane et al., Bull. Chem. Soc. Jap. 42 (1969), 3204.
Volkamer et al., (1967) Angewandte Chemie 79 (21): 941–942.

*Primary Examiner*—Paul R. Michl
*Assistant Examiner*—Cynthia Hamilton
*Attorney, Agent, or Firm*—Keil & Weinkauf

[57] ABSTRACT

Phenanthroimidazole compounds, a process for their preparation, photopolymerizable coating and recording materials and lithographic layers produced using these.

The novel phenanthroimidazole compounds are useful as photoinitiators for photopolymerizable coating and recording materials.

7 Claims, No Drawings

PHENANTHROIMIDAZOLE COMPOUNDS, THEIR PREPARATION, PHOTOPOLYMERIZABLE COATING AND RECORDING MATERIALS, AND LITHOGRAPHIC LAYERS PRODUCED USING THESE

The present invention relates to phenanthroimidazole compounds, a process for their preparation, photopolymerizable coating and recording materials which contain these phenanthroimidazole compounds as photoinitiators, layers for the production of printing plates for letterpress or gravure printing or for etching.

Photopolymerizable mixtures and coating and recording materials produced from them have been used for the production of relief printing plates, lithographic printing plates, printed circuits etc. For these applications, these photopolymerizable coating and recording materials are exposed to actinic light, thus curing the layer, which is usually a mixture of polymeric binder with one or more monomers having one or more photopolymerizable olefinically unsaturated double bonds.

In the photopolymerization of ethylenically unsaturated compounds, there are many known initiators for increasing the rate of polymerization. Some of these initiators are 1,2-dicarbonyl compounds, for example diacetyl and benzil, other initiators being α-hydrocarbonsubstituted aromatic acyloins, eg. α-methylbenzoin, polynucler quinones and a combination of free radical-donating substances and 2,4,5-triphenylimidazolyl dimers. In searching for novel initiators which possess a very high spectrosensitivity and a very long shelf life, even when exposed to heat, and have a relatively low volatility, which is particularly important in thin layers, we have found, surprisingly, that, when exposed to actinic light, specific hydroxyl-substituted phenanthroimidazoles are converted to reactive species which initiate the photopolymerization of ethylenically unsaturated monomers.

The present invention relates to phenanthroimidazole compounds of the general formula (I) or (II)

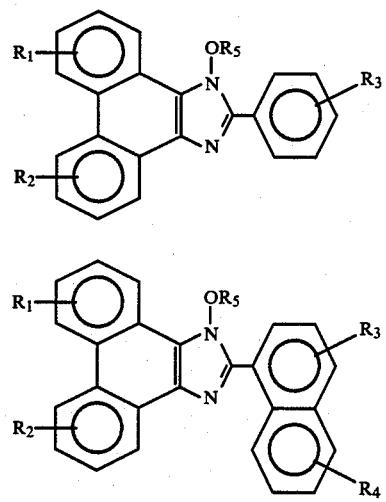

where $R_1$, $R_2$, $R_3$ and $R_4$ are identical or different and are each hydrogen, alkyl, alkoxy, halogen or amino, $R_5$ is alkyl, alkoxy, aralkyl, alkylsulfonyl, arylsulfonyl, dialkoxyphosphoryl, dialkylphosphoryl, diarylphosphoryl or a carbonyl radical

and $R_6$ is alkyl, alkoxy, phenyl or dialkylamino. Particularly preferred phenanthroimidazole compounds of the formula (I) or (II) are those in which $R_5$ is

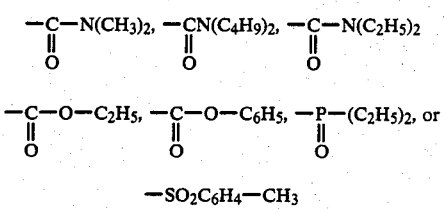

The present invention furthermore relates to a process for the preparation of these phenanthroimidazole compounds, wherein the corresponding 1-hydroxy-2-arylphenanthroimidazole is reacted with an appropriate electrophilic reagent. The present invention furthermore relates to photopolymerizable coating and recording materials which contain one or more photopolymerizable olefinically unsaturated organic compounds, a photoinitiator and, if required, further assistants and additives, the said coating and recording materials containing one of the novel phenanthroimidazole compounds as the photoinitiator. In a particular embodiment of the invention, the photopolymerizable coating and recording materials additionally contain a polymeric binder.

The present invention also relates to a process for the production of photoresists or offset printing plates and for the production of printing plates for letterpress printing, gravure printing or the etching technique, using the photopolymerizable coating and recording materials as a lithographic layer. The novel phenanthroimidazole compounds are distinguished by a very long shelf life, good compatibility with polymeric binders and low volatility.

Regarding the novel compounds, their preparation and their use, the following may be stated specifically.

The phenanthroimidazole compounds are compounds of the general formula (I) or (II)

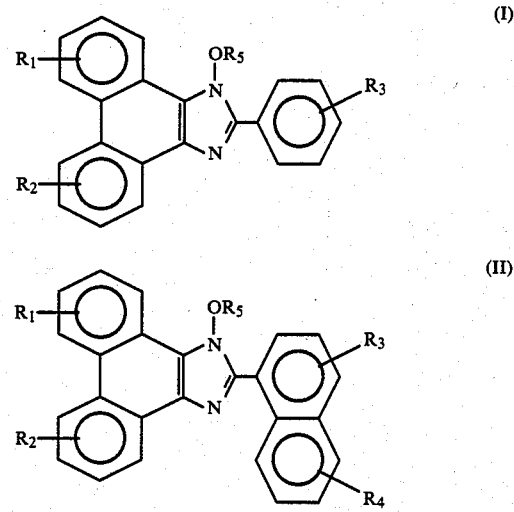

where $R_1$, $R_2$, $R_3$ and $R_4$ are identical or different and are each hydrogen, alkyl, alkoxy, halogen or amino, $R_5$ is alkyl, alkoxy, aralkyl, alkylsulfonyl, arylsulfonyl, dialkoxyphosphoryl, dialkylphosphoryl, diarylphosphoryl or a carbonyl radical

and $R_6$ is alkyl, alkoxy, phenyl or dialkylamino.

Suitable alkyl radicals $R_1$, $R_2$, $R_3$, $R_4$ and $R_5$ are straight-chain or branched alkyl of 1 to 18, preferably 1 to 6, carbon atoms or cyclohexyl, eg. methyl, ethyl, n-propyl, isopropyl, n-butyl, isobutyl, tert.-butyl, pentyl, hexyl, heptyl, octyl, isooctyl, 2-ethylhexyl, decyl, undecyl, dodecyl or stearyl; suitable alkoxy radicals $R_1$, $R_2$, $R_3$, $R_4$ and $R_5$ are straight-chain or branched alkoxy of 1 to 18, preferably 1 to 6, carbon atoms, eg. methoxy, ethoxy, propoxy, butoxy, pentyloxy or hexyloxy; suitable halogen radicals $R_1$, $R_2$, $R_3$ and $R_4$ are fluorine, chlorine, bromine and iodine, preferably chlorine; suitable amino radicals $R_1$, $R_2$, $R_3$ and $R_4$ are —NH$_2$ and mono- and dialkylamino where alkyl is of 1 to 6 carbon atoms; and suitable aralkyl radicals $R_5$ are, for example, benzyl radicals. Carbonyl radicals $R_5$ of the formula

where $R_6$ is alkyl of 1 to 18, preferably 1 to 12, carbon atoms, alkoxy of 1 to 18, preferably 1 to 6, carbon atoms, phenyl or dialkylamino where alkyl is of 1 to 6 carbon atoms are, for example, methyl, butyl, trimethylphenyl or toluyl; examples of suitable alkylsulfonyl radicals $R_5$ are those where alkyl is of 1 to 18, preferably 1 to 6, carbon atoms; examples of suitable arylsulfonyl radicals $R_5$ are phenylsulfonyl and 4-methylphenylsulfonyl; examples of suitable dialkoxyphosphoryl and dialkylphoshoryl radicals $R_5$ are those where alkoxy or alkyl is of 1 to to 12, preferably 1 to 6, carbon atoms; and an example of a suitable diarylphosphoryl radical $R_5$ is diphenylphosphoryl.

Examples of preferred novel photoinitiators of the formula (I) or (II) are:
1-acetoxy-2-phenylphenanthroimidazole,
1-acetoxy-2-(2-chlorophenyl)phenanthroimidazole,
1-(N,N-dibutylaminocarbonyloxy)-2-phenylphenanthroimidazole and
1-benzoyloxy-2-phenylphenanthroimidazole.

The particular 1-hydroxy-2-aryl-phenanthroimidazoles are prepared by a conventional method, for example as described by:
F. J. Allan and G. G. Allan, Chem. Ind. 1964, 1837;
K. Volkamer and H. W. Zimmermann, Chem. Ber. 102 (1969), 4177 or
K. Akagane et al., Bull. Chem. Soc. Jap. 42 (1969), 3204.

The reaction of these 1-hydroxy-2-arylphenanthroimidazoles with electrophilic reagents is advantageously carried out either directly in a suitable solvent or in the presence of a basic compound.

The photopolymerizable coating and recording materials contain one or more photopolymerizable olefinically unsaturated organic compounds, preferably those having a boiling point higher than 150° C., in particular a mixture of low molecular weight and high molecular weight compounds of this type, and the novel phenanthroimidazole compounds, in general in amounts of from 0.1 to 20, preferably from 0.2 to 5%, by weight, based on the total amount of photopolymerizable olefinically unsaturated organic compounds. They may also contain other assistants and additives, eg. amines, in particular leuco dyes, for example those from the groups consisting of
aminotriarylmethane compounds,
aminoxanthene compounds,
aminothioxanthene compounds,
amino-9,10-dihydroacridine compounds,
aminophenoxazine compounds,
aminophenothiazine compounds,
aminodihydrophenazine compounds,
aminodiphenylmethane compounds,
leucoindamine compounds,
aminohydrocinnamic acids,
hydrazines,
leuco indigoid dyes,
amino-2,3-dihydroanthraquinones,
tetrahalo-p,p-biphenols,
2-(p-hydroxyphenyl)-4,5-diphenylimidazoles and
phenethylaniline compounds, such as crystal violet leuco base.

Amines and leuco dyes can be added, for example, in amounts of from 0.1 to 2% by weight, based on the binder.

Particularly suitable polymeric binders are film-forming polymers, such as homopolymers and copolymers, provided that they have the properties desired for the particular field of use, for example homopolymers and copolymers of acrylates or methacrylates of monoalkanols of 1 to 8 carbon atoms, eg. methanol, butanol or 2-ethylhexanol, copolymers of vinylaromatics, such as those of styrene or vinyltoluene, vinyl ester copolymers, vinyl chloride and vinylidene chloride copolymers, partially hydrolyzed polyvinyl acetate, N-vinylpyrrolidone (co)polymers, olefin/(meth)acrylate copolymers and olefin/vinyl ester copolymers, suitable olefins being ethylene, propylene and butadiene, preferably ethylene.

These copolymers may also contain functional groups, such as —COOH and/or —OH and —NH$_2$ as a result of incorporating, as copolymerized units, monomers possessing corresponding groups. Other suitable film-forming polymers are polycondensates and polyadducts, such as polyesters, polyurethanes and in particular nylons. Particularly preferred film-forming polymers, which are usually applied in the form of their solution to the substrate to be coated, for example a polyester film or aluminum sheet, and are dried, are, for example, copolymers of methyl methacrylate, acrylic acid and hydroxypropyl acrylate.

The other conventional additives vary depending on the specific intended use.

Where the layers in question are photopolymerizable ones, they contain photopolymerizable monomers, such as polyfunctional acrylates and/or methacrylates, such as the esters of acrylic or methacrylic acid with dihydric or polyhydric alcohols, such as ethylene glycol, propylene glycol, butanediol, hexanediol, trimethylolpropane, glycerol, pentaerythritol or the like, the reaction products of (poly)epoxide compounds with (meth)acrylic acid, urethane acrylates, unsaturated polyesters and mixtures of the stated functional compounds with monofunctional compounds, such as esters of acrylic acid or methacrylic acid with $C_1$–$C_8$-monoalkanols, vinyl esters, vinylaromatics and/or N-vinyllactams, eg. N-vinylpyrrolidone.

Other additives are assistants and additives such as stabilizers and sensitizers, which are generally used in minor amounts.

The novel photopolymerizable coating and recording materials can be used, for example, for the production of lithographic layers for photoresists, offset, letterpress and gravure printing and etching (for example on glass or aluminum). These processes are described in, for example, German Laid-Open Applications DOS No. 3,231,145, DOS No. 3,231,147, DOS No. 3,331,691 and DOS No. 3,231,144 and in Günther Herrmann, Leiterplatten, Lenze-Verlag, Stuttgart, 1978 in the case of the photoresist sector.

The novel photochromic systems are distinguished in particular by a very long shelf life, compatibility with polymeric binders and their low volatility. They are particularly useful for negative-working photoresist films.

In the comparative example and in the Examples, parts and percentages are by weight, unless stated otherwise.

EXAMPLE 1

Preparation of 1-acetoxy-2-(2-chlorophenyl)-phenanthroimidazole 4 parts of 1-hydroxy-2-(2-chlorophenyl)-phenanthroimidazole in 30 parts of tetrahydrofuran are initially taken, and 2 parts of pyridine and 3.6 parts of acetic anhydride are then added. The mixture is stirred for five hours at room temperature, after which 40 parts of ethyl acetate are added to the resulting solution. The organic phase thus obtained is washed several times with water and dried over sodium sulfate, after which the solvent is stripped off. The solid which remains is recrystallized from methyl ethyl ketone/cyclohexane.

3.5 parts of a solid which has a melting point of 140° C. and gives the following analytical data are obtained:
Analysis: Calculated: C 71.4, H 3.9, N 7.2, Cl 9.2. Found: C 71.3, H 4.1, N 7.2, Cl 9.2.

EXAMPLE 2

Preparation of 1-(N,N-dibutylaminocarbonyloxy)-2-phenylphenanthroimidazole 10 parts of 1-hydroxy-2-phenylphenanthroimidazole, 8 parts of anhydrous potassium carbonate and 6.7 parts of N,N-dibutylcarbamyl chloride in 100 parts of tetrahydrofuran are refluxed for 5 hours. 100 parts of water and 200 parts of ethyl acetate are then added. The organic phase is washed with water, dried over sodium sulfate and evaporated down under reduced pressure. When the residue is left to stand, 6.6 parts of a solid which has a melting point of 120° C. and is pure according to thin layer chromatography are obtained.

PRODUCTION OF PHOTORESIST FILMS

Comparative Example

A mixture consisting of 55 parts of polymethyl methacrylate (eg. Degalan ® LP 50/09), 18 parts of trimethylolpropane triacrylate, 13.5 parts of butanediol diacrylate, 9.4 parts of p-toluenesulfonamide, 0.45 part of crystal violet leuco base, 0.13 part of Michler's ketone, 3 parts of benzophenone and 3 parts of hexachloroxylene in 155 parts of ethyl acetate was prepared. The solution was stirred for four hours, filtered through a pressure filter having a pore diameter of 1 μm and then applied as a layer on a 0.023 mm thick polyester film (eg. Melinex ® S 23 from ICI) in an amount such that, after drying with warm air, a resist film 0.035 mm thick remained.

The resist film was laminated with brushed copper in a conventional laminator (eg. in Riston, HOT-ROLL laminator HRL 24). The photoresist was then exposed in a commercial Riston B24 processor through the photographic transparency of an electrical circuit diagram and of the nylotron ® stepwedge for 10 cycles. Color contrast between exposed and unexposed image areas was obtained. After development of the photoresist (for 30 minutes with trichloroethane at 18° C.) an image up to nylotron stepwedge 8 was obtained.

EXAMPLE 3

As described in the comparative example, a resist film was produced using 2.5 parts of 1-acetoxy-2-(2-chlorophenyl)-phenanthroimidazole instead of 0.13 part of Michler's ketone, 3 parts of benzophenone and 3 parts of hexachloroxylene.

This photoresist was likewise exposed for 10 cycles in a Riston B 24 processor through the photographic transparency of the nylotron ® stepwedge. After development of the photoresist (for 30 minutes with trichloroethane at 18° C.), an image up to nylotron ® stepwedge 5 was obtained.

EXAMPLE 4

In the production of a photoresist film by a method similar to that described in Example 3, the photoinitiator 1-(N,N-dibutylaminocarbonyloxy)-2-phenylphenanthroimidazole behaved similarly to the initiator used in Example 3. Exposure for 10 cycles and development gave stepwedge 6.

We claim:
1. A phenanthroimidazole compound of the formula (I) or (II)

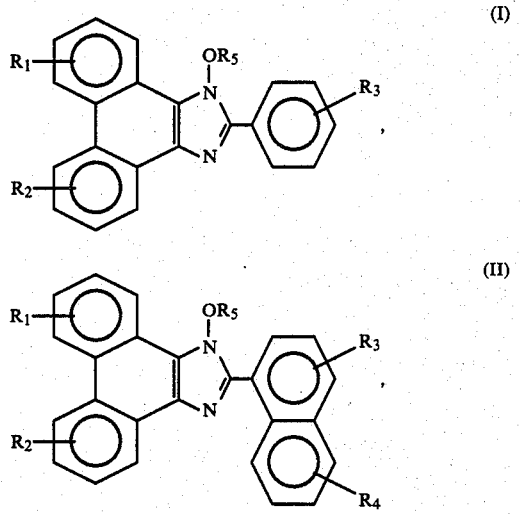

where R₁, R₂, R₃ and R₄ are identical or different and are each hydrogen, alkyl, alkoxy, halogen or amino, R₅ is alkyl, alkoxy, aralkyl, alkylsulfonyl, arylsulfonyl, dialkoxyphosphoryl, dialkylphosphoryl, diarylphosphoryl or a carbonyl radical

and $R_6$ is alkyl, alkoxy, phenyl or dialkylamino.

2. A photopolymerizable coating and recording material which comprises: one or more photopolymerizable olefinically unsaturated organic compounds and a photoinitiator, wherein the photoinitiator is a phenanthroimidazole compound as defined in claim 1.

3. A photopolymerizable coating and recording material as claimed in claim 2, which additionally contains a polymeric binder.

4. A photopolymerizable coating and recording material as claimed in claim 2, wherein the photoinitiator used is a phenanthroimidazole compound of the formula (I) or (II) as claimed in claim 1, where $R_5$ is

-continued

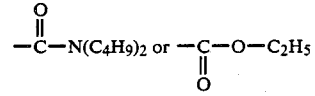

5. A photopolymerizable coating and recording material as claimed in claim 3, wherein the photoinitiator used is a phenanthroimidazole compound of the formula (I) or (II) according to claim 1, where $R_5$ is

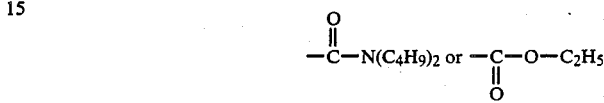

6. A photopolymerizable coating and recording material as set forth in claim 3, wherein the material contains a stabilizer.

7. A photopolymerizable coating and recording material as set forth in claim 3, wherein the material contains a sensitizer.

* * * * *